(12) United States Patent
Bohn et al.

(10) Patent No.: US 7,220,345 B2
(45) Date of Patent: May 22, 2007

(54) HYBRID MICROFLUIDIC AND NANOFLUIDIC SYSTEM

(75) Inventors: Paul W. Bohn, Champaign, IL (US); Jonathan V. Sweedler, Urbana, IL (US); Mark A. Shannon, Champaign, IL (US); Tzu-chi Kuo, Savoy, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 390 days.

(21) Appl. No.: 10/273,935

(22) Filed: Oct. 18, 2002

(65) Prior Publication Data

US 2003/0136679 A1    Jul. 24, 2003

Related U.S. Application Data

(60) Provisional application No. 60/330,417, filed on Oct. 18, 2001.

(51) Int. Cl.
*B67D 5/00*    (2006.01)
(52) U.S. Cl. ........................ 204/600; 422/100
(58) Field of Classification Search ................ 204/600, 204/450; 422/100; 137/833; 210/321.75
See application file for complete search history.

(56) References Cited

U.S. PATENT DOCUMENTS

| | | | |
|---|---|---|---|
| 5,556,528 A * | 9/1996 | Bohn et al. ............... | 204/600 |
| 5,890,745 A | 4/1999 | Kovacs | |
| 5,965,001 A | 10/1999 | Chow et al. | |
| 6,086,740 A | 7/2000 | Kennedy | |
| 6,103,199 A * | 8/2000 | Bjornson et al. ........... | 422/100 |
| 6,129,973 A | 10/2000 | Martin et al. | |
| 6,607,644 B1 * | 8/2003 | Apffel, Jr. .................. | 204/451 |
| 6,806,543 B2 * | 10/2004 | Yamakawa et al. ......... | 257/414 |
| 6,878,271 B2 * | 4/2005 | Gilbert et al. ......... | 210/321.61 |
| 2003/0180711 A1 * | 9/2003 | Turner et al. .................. | 435/4 |

FOREIGN PATENT DOCUMENTS

WO    WO 95/11755    *    5/1995

OTHER PUBLICATIONS

Terry et al., "A Gas Chromatographic Air Analyzer Fabricated on a Silicon Wafer," IEEE Transactions on Electron Devices, 1979, pp. 1880-1886, vol. ED-26, No. 12.

(Continued)

*Primary Examiner*—Kaj K. Olsen
(74) *Attorney, Agent, or Firm*—Evan Law Group LLC

(57) ABSTRACT

A fluid circuit includes a membrane having a first side, a second side opposite the first side, and a pore extending from the first side to the second side. The circuit also includes a first channel containing fluid extending along the first side of the membrane and a second channel containing fluid extending along the second side of the membrane and crossing the first channel. The circuit also includes an electrical source in electrical communication with at least one of the first fluid and second fluid for selectively developing an electrical potential between fluid in the first channel and fluid in the second channel. This causes at least one component of fluid to pass through the pore in the membrane from one of the first channel and the second channel to the other of the first channel and the second channel.

71 Claims, 8 Drawing Sheets

OTHER PUBLICATIONS

Manz et al., "Miniaturized Total Chemical Analysis Systems: A Novel Concept for Chemical Sensing," Sensors and Actuators B, 1990, pp. 244-248, vol. 1, Issues 1-6.

Van Der Schoot et al., "A Silicon Integrated Miniature Chemical Analysis System," Sensors and Actuators B, 1992, pp. 57-60, vol. 6, Issues 1-3.

Harrison et al., "Micromachining a Miniatruized Capillary Electrophoresis-Based Chemical Analysis System on a Chip," Science, 1993, pp. 895-897, vol. 261, Issue 5123.

Fettinger et al., "Stacked Modules for Micro Flow Systems in Chemical Analysis: Concept and Studies Using an Enlarged Model," Sensors and Actuators B, 1993, pp. 19-25, vol. 17, Issue I.

Jacobson et al., "Effects of Injection Schemes and Column Geometry on the Performance of Microchip Electrophoresis Devices," Anal. Chem., 1994, pp. 1107-1113, vol. 66.

Verpoorte et al., "Three-Dimensional Mirco Flow Manifolds for Miniaturized Chemical Analysis Systems", J. Micromech, Microeng., 1994, pp. 246-256, vol. 4.

Seller et al., "Electroosmotic Pumping and Valveless Control of Fluid Flow Within a Manifold of Capillaries on a Glass Chip," Anal. Chem., 1994, pp. 3485-3491, vol. 66.

Wooley et al., "Ultra-High-Speed DNA Fragment Separations Using Microfabricated Capillary Array Electrophoresis Chips," Proceedings of the National Academy of Sciences of the United States of America, 1994, pp. 11348-11352, vol. 91, Issue 24.

Jirage et al., "Nanotubule-Based Molecular-Filtration Membranes," Science, 1997, pp. 655-658, vol. 278.

Jaeggi et al., "Novel Interconnection Technologies for Integrated Microfluidic Systems," Solid-State Sensor and Actuator Workshop, Hilton Head Island, SC, 1998, pp. 112-115.

Christel et al., "High Aspect Ratio Silicon Microstructures for Nucleic Acid Extraction," Solid-State Sensor and Actuator Workshop, Hilton Head Island, SC, 1998, pp. 363-366.

Man et al., "Microfabricated Capillarity-Driven Stop Valve and Sample Injector," IEEE Transactions, 1998, pp. 45-50, vol. unknown.

Lee et al., "High Aspect Ratio Polymer Microstructures and Cantilevers for BioMEMS Using Low Energy Ion Beam and Photolithography," Sensors and Actuators A, 1998, pp. 144-149, vol. 71.

Gonzalez et al., "MicroJoinery: Concept, Definition, and Application to Microsystem Development," Sensors and Actuators A, 1998, pp. 315-332, vol. 66.

Hong et al., "Selectively-Permeable Ultrathin Film Composite Membranes Based on Molecularly-Imprinted Polymers," Chem. Mater., 1998, pp. 1029-1033, vol. 10.

Yang et al., "Micromachined Membrane Particle Filters," Sensors and Actuators, 1999, pp. 184-191, vol. 73.

Koch et al., "Micromachined Chemical Reaction System," Sensors and Actuators, 1999, pp. 207-210, vol. 74.

Duffy et al., "Rapid Prototyping of Microfluidic Switches in Poly(dimethyl siloxane) and Their Actuation by Electro-Osmotic Flow," J. Micromech. Microeng., 1999, pp. 211-217, vol. 9.

Gray et al., "Novel Interconnection Technologies for Integrated Microfluidic Systems," Sensors and Actuators, 1999, pp. 57-65, vol. 77.

Jacobson et al., "Microfluidic Devices for Electrokinetically Driven Parallel an Serial Mixing," Anal. Chem., 1999, pp. 4455-4459, vol. 71.

Haab et al., "Single-Molecule Detection of DNA Separations in Microfabricated Capillary Electrophoresis Chips Employing Focused Molecular Streams," Anal. Chem., 1999, pp. 5137-5145, vol. 71.

Jirage et al., "Effect of Thiol Chemisorption on the Transport Properties of Gold Nanotubule Membranes," Anal. Chem., 1999, pp. 4913-4918, vol. 71, No. 21.

Jo et al., "Fabrication of Three-Dimensional Microfluidic Systems by Stacking Molded Polydimethylsiloxane (PDMS) Layers," SPIE, 1999, pp. 222-229, vol. 3877.

Folch et al., "Molding of Deep Polydimethylsiloxane Microstructures for Microfluidics and Biological Applications," Transactions of the ASME, 1999, pp. 28-34, vol. 121.

Becker et al., "Polymer Microfabrication Methods for Microfluidic Analytical Applications," Electrophoresis 2000, 2000, pp. 12-26, vol. 21.

McDonald et al., "Fabrication of Microfluidic Systems in Poly(dimethysiloxane)," Electrophoresis 2000, 2000, pp. 27-40, vol. 21.

Anderson et al., "Fabrication of Topologically Complex Three-Dimensional Microfluidic Systems in PDMS by Rapid Prototyping," Anal. Chem. 2000, 2000, pp. 3158-3164, vol. 72.

Chiu et al., "Patterned Deposition of Cells and Proteins Onto Surfaces by Using Three-Dimensional Microfluidic Systems," Proc. Natl. Acad. Sci. USA, 2000, pp. 2408-2413, vol. 97, Issue 6.

Dharmatilleke et al.,"Three dimensional Silicone Device Fabrication and Interconnection Scheme for Microfluidic Applications Using Sacrificial Wax Layers," MEMS, 2000, pp. 413-418, vol. 2.

Jo et al., "Three-Dimesional Mirco-Channel Fabrication in Polydimethylsiloxane (PDMS) Elastomer," Journal of Microlectromechanical Systems, 2000, pp. 76-81, vol. 9, No. 1.

Dharmatilleke et al., "Three-Dimensional Silicone Microfluidic Interconnection Scheme Using Sacrificial Wax Filaments," Proceedings of SPIE, 2000, pp. 90-97, vol. 4177.

Chu et al., "Using Three-Dimensional Microfluidic Networks for Solving Computationally Hard Problems," Proc. Natl. Acad. Sci. USA, 2001, pp. 2961-2966, vol. 98, Issue 6.

Lee et al., "pH-Switchable, Ion-Permselective Gold Nanotubule Membrane Based on Chemisorbed Cysteine," Anal. Chem., 2001, pp. 768-775, vol. 73.

Kugelmass et al., "Fabrication and Characterization of Three-Dimensional Microfluidic Arrays," Orchid Biocomputer, Inc., Princeton, NJ, pp. 88-94.

Hulteen, J., K. Jirage, and C. Martin, "Introducing Chemical Transport Selectivity into Gold Nanotubule Membranes," *J. Am. Chem. Soc.*, 120:6603-6604 (1998).

Martin, P., D. Matson, W. Bennett, and D. Hammerstrom, "Fabrication of plastic microfluidic components," *SPIE*, 3515:172-176 (1998).

Kuo, T-C., et al., "Manipulating molecular transport through nanoporous membranes by control of electrokinetic flow: Effect of surface charge density and debye length"., Langmuir, vol. 17, No. 20, pp. 6298-6303, Sep. 8, 2001.

* cited by examiner

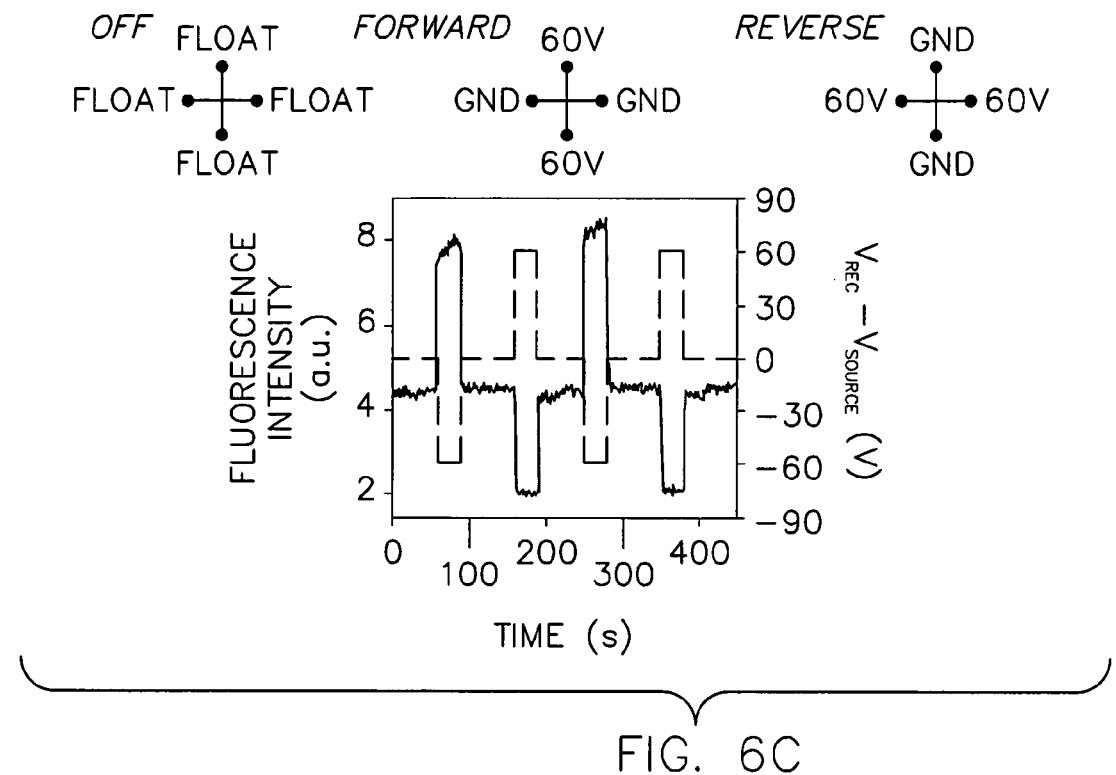
FIG. 6C
FIG. 6D
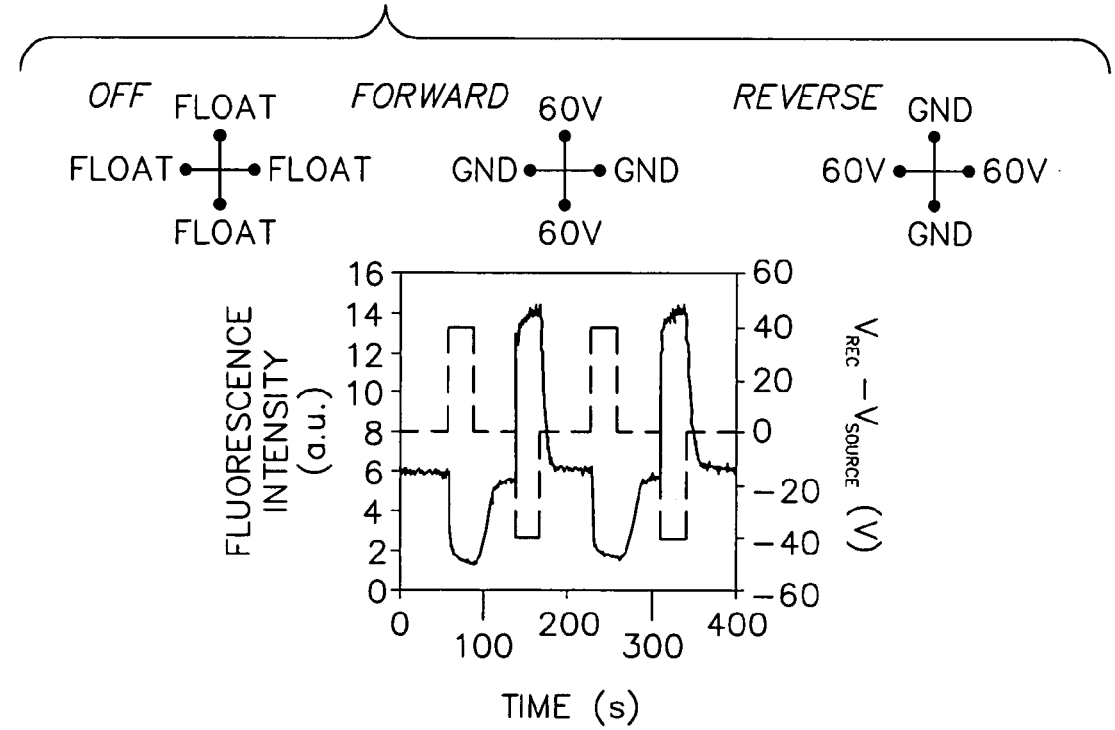

HYBRID MICROFLUIDIC AND NANOFLUIDIC SYSTEM

This application claims priority from U.S. Provisional Patent Application No. 60/330,417 filed Oct. 18, 2001, which is hereby incorporated by reference.

This invention was made with government support under grants from the U.S. Department of Energy (DE FG02 88ER13949 and DE FG02 99ER62797), the U.S. Defense Advanced Research Projects Agency (F30602-00-2-0567) and the National Cancer Institute (CA82081). The U.S. government has certain rights in this invention.

BACKGROUND OF THE INVENTION

The present invention relates generally to a microfluidic system, and more particularly to a microfluidic system having an externally controllable nanofluidic interconnect.

Microfluidic devices are devices for controlling fluid flow having dimensions less than about one millimeter. These devices are becoming increasingly important in chemical and biochemical sensing, molecular separations, drug delivery and other emerging technologies. New microfluidic devices and methods for rapidly constructing these devices are being developed. However, most prior art devices are two-dimensional. To produce three-dimensional microfluidic devices, interconnects between two-dimensional structures often are made. However, creation of these interconnects has proved challenging. Many prior three-dimensional microfluidic devices use discrete channels to bridge, rather than connect, independent analysis modules. In other words, the channels passively connect the modules and do not have gates or valves for selectively permitting and preventing flow from one module to the next. Although a pressure activated valve has been developed, this interconnect has limited usefulness because it depends on a variation in pressure of the fluid for opening and closing the valve. Thus, there is a need for an externally controllable active interconnect to exploit the full three-dimensional capacity of microfluidic devices.

SUMMARY OF THE INVENTION

Briefly, the present invention includes a fluid circuit comprising a membrane having a first side, a second side opposite the first side, and a pore extending from the first side to the second side. The fluid circuit also includes a first channel containing fluid extending along the first side of the membrane and a second channel containing fluid extending along the second side of the membrane and crossing the first channel. Further, the circuit comprises an electrical source in electrical communication with at least one of the first fluid and second fluid for selectively developing an electrical potential between fluid in the first channel and fluid in the second channel thereby causing at least one component of fluid to pass through the pore in the membrane from one of the channels to the other.

In another aspect, the invention includes a fluid circuit comprising a membrane having a pore having a width less than about 250 nanometers, a first channel containing fluid extending along the first side of the membrane, and a second channel containing fluid extending along the second side of the membrane.

In yet another aspect, the invention includes a circuit comprising a membrane, a first channel containing a first fluid having a first Debye length in fluid communication with the first side of the membrane, and a second channel containing a second fluid having a second Debye length at least as long as the first Debye length in fluid communication with the second side of the membrane. The pore in the membrane has a width between about 0.01 and about 1000 times the first Debye length.

Apparatus of the present invention for constructing a fluid circuit comprises a membrane, a first channel for containing fluid in fluid communication with a first side of the membrane, and a second channel for containing fluid in fluid communication with the second side of the membrane. Further, the apparatus includes an electrical source in electrical communication with at least one of the first channel and the second channel for selectively developing an electrical potential between fluid in the first channel and fluid in the second channel thereby causing at least one component of fluid to pass through the pore in the membrane from one channel to the other.

A method of the present invention for isolating a particle having a selected electrophoretic velocity from a plurality of particles using the apparatus described above comprises filling the first channel with a fluid, positioning the plurality of particles in the fluid at a first end of the first channel, and developing an electrical potential between the first end of the first channel and a second end of the first channel opposite the first end so the plurality of particles migrate along the first channel from the first end to the second end in an order corresponding to their respective electrophoretic velocities. An electrical potential is developed between the first channel and the second channel when the particle having the selected electrophoretic velocity is adjacent the pore in the membrane so the particle passes through the pore from the first channel to the second channel.

In another method of the present invention, at least one component of fluid is transferred from a first channel to a second channel. Fluid is delivered to the first channel extending along a first side of a membrane and to the second channel extending along a second side of the membrane. An electrical potential is developed between the fluid in the first channel and the fluid in the second channel thereby causing at least one component of fluid to pass through the pore in the membrane.

In yet another method of the present invention, a selected component within a fluid comprising a plurality of components is tagged. A chemical reagent is passed through the pore so the reagent coats a surface of the pore. The pore is flushed to remove the reagent from a central portion of the pore so at least a portion of the reagent coating remains on the surface of the pores. At least one component of the fluid is passed through the pore so the selected component contacts the reagent.

Another apparatus of the present invention comprises a plurality of membranes, each having a first side, a second side opposite the first side, and a pore extending from the first side to the second side. The apparatus also includes a plurality of pairs of channels, each including a first channel adjacent at least one of the first sides of the membranes for containing fluid in fluid communication with the first side of the respective membrane and a second channel adjacent at least one of the second sides of the membranes for containing fluid in fluid communication with the second side of the respective membrane. In addition, the apparatus includes an electrical source in electrical communication with at least one of the channels for selectively developing an electrical potential between fluid in at least two of the channels thereby causing at least one component of fluid to pass through the pore in at least one of said membranes.

Other features of the present invention will be in part apparent and in part pointed out hereinafter.

BRIEF DESCRIPTION OF THE DRAWINGS

FIGS. 6a–6d are fluorescence signature graphs for various experimental transfers;

Corresponding reference characters indicate corresponding parts throughout the several views of the drawings.

DETAILED DESCRIPTION OF THE PREFERRED EMBODIMENT

Figure 1:
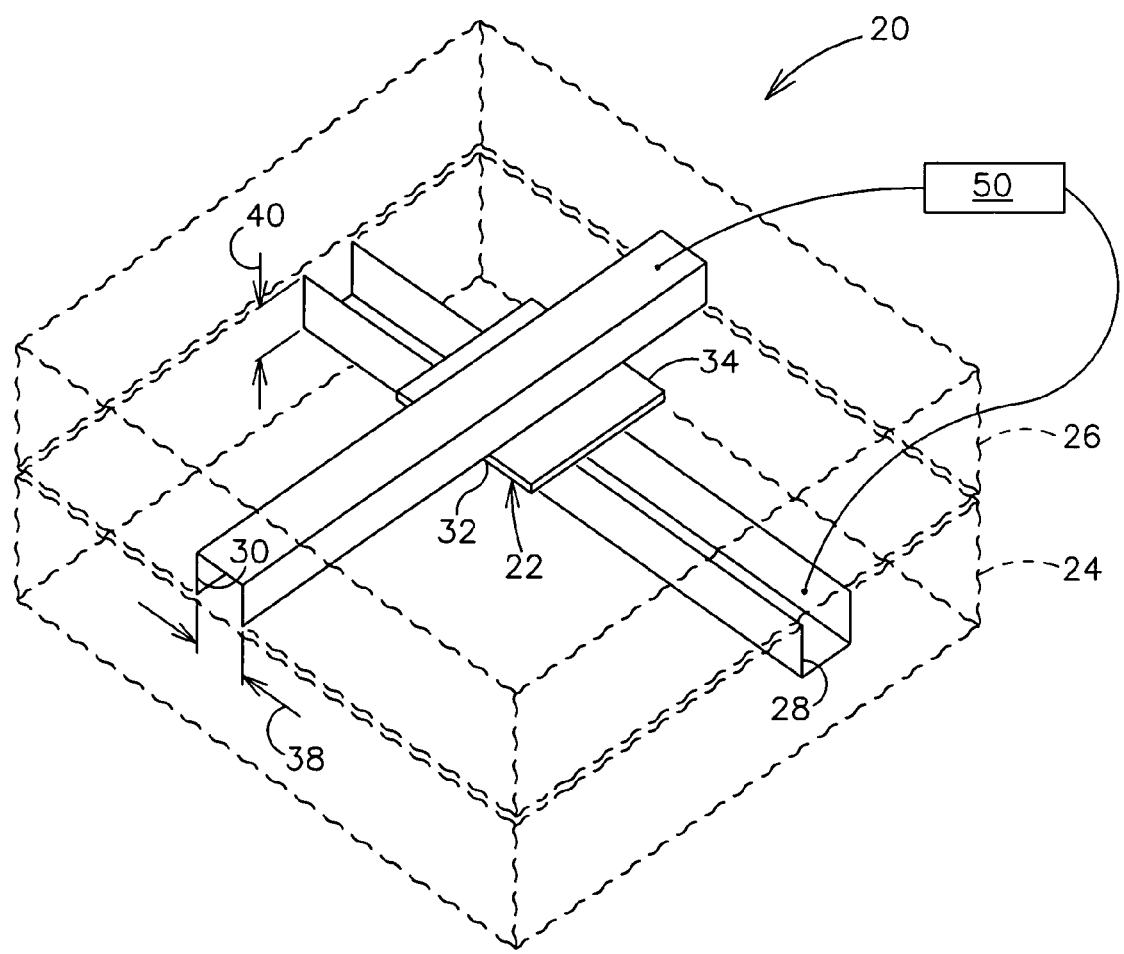
FIG. 1 is a schematic perspective of an apparatus of the present invention showing bodies of the apparatus in phantom for clarity.

Referring now to the drawings and in particular to FIG. 1, apparatus of the present invention is designated in its entirety by the reference numeral 20. The apparatus 20 generally comprises a porous membrane, generally designated by 22, positioned between first and second bodies 24, 26 having first and second channels 28, 30, respectively, formed therein. The membrane 22 has a first side 32 facing the first body 24 and a second side 34 opposite the first side facing the second body. The first channel 28 is formed in the first body 24 so it extends along the membrane 22 adjacent the first side 32 of the membrane. Similarly, the second channel 30 is formed in the second body 26 so it extends along the membrane 22 adjacent the second side 34 of the membrane. As will be explained in further detail below, the first and second channels 28, 30 each contain fluid in communication with the respective side of the membrane 22. In one particularly useful embodiment of the present invention, the first and second channels 28, 30 cross at an angle. In one embodiment, the first and second channels 28, 30 are straight and extend perpendicular to each other. Although the first and second bodies 24, 26 may be made of other materials without departing from the scope of the present invention, in one embodiment they are made of polydimethylsiloxane (PDMS). Although the channels 28, 30 may be made using other techniques without departing from the scope of the present invention, in one embodiment the channels are made using standard rapid prototyping techniques commonly used for PDMS. Such techniques are described in J. C. McDonald, *Electrophoresis* 21, 27 –40 (2000). Although the resulting channels 28, 30 may have other dimensions without departing from the scope of the present invention, in one embodiment each channel has a width 38 of about 100 micrometer (um) and a depth 40 of about 30 um.

Figure 2:
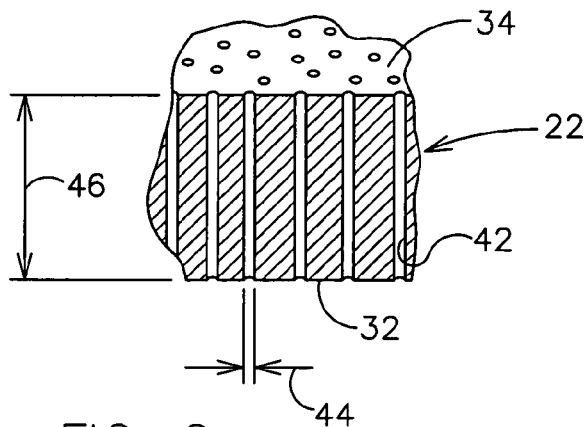
FIG. 2 is detail of a membrane portion of the apparatus of the present invention.

As illustrated in FIG. 2, the nanoporous membrane 22 has at least one pore (and preferably a plurality of pores) 42 extending from the first side 32 of the membrane to the second side 34 of the membrane. As illustrated in FIG. 2, the pores 42 in one embodiment each have a width 44 less than about 250 nanometers (nm). In one embodiment, the membrane 22 has a monodisperse distribution of pore widths 44. In one particularly useful embodiment, each pore 42 has a width 44 between about 10 nm and about 230 nm. In still another embodiment, each pore 42 has a width 44 between about 15 nm and about 220 nm. In most embodiments, the pores 42 are generally cylindrical and the width 44 is a diameter of the cylinder. Although the membrane 22 may have other pore densities without departing from the scope of the present invention, in one embodiment the membrane has a pore density of between about 1,000,000 pores per square centimeter and about 10,000,000,000 pores per square centimeter. In one particularly useful embodiment, the membrane 22 has a pore density of between about 100,000,000 pores per square centimeter and about 600,000,000 pores per square centimeter. Although the membrane 22 may have other thicknesses without departing from the scope of the present invention, in one embodiment the membrane 22 has a thickness 46 between about 1 um and about 100 um. In one particularly useful embodiment, the membrane 22 has a thickness 46 of about 10 um. Although the membrane 22 may be made of other materials without departing from the scope of the present invention, in one embodiment the membrane is made of nuclear track etched polycarbonate film (PCTE). One such membrane 22 is available from Osmonics, Inc. of Minnetonka, Minn. Such membranes have been used as active components in bulk solution experiments to trap and selectively move molecules.

As illustrated in FIG. 1, an electrical source 50 is positioned in electrical communication with at least one of the channels 28, 30 for selectively developing an electrical potential between fluid in the first channel and fluid in the second channel. As will be appreciated by those skilled in the art, when the electrical potential is of the proper polarity and magnitude, it causes one or more components (e.g., charged particles or molecules) within the fluid to pass through the pore 42 in the membrane 22 from one of the channels 28, 30 to the other by electrokinetic flow. Although other electrical potentials may be developed by the electrical source 50 without departing from the scope of the present invention, in one embodiment the potential is between about 10 millivolts and about 200 volts.

Figure 3:
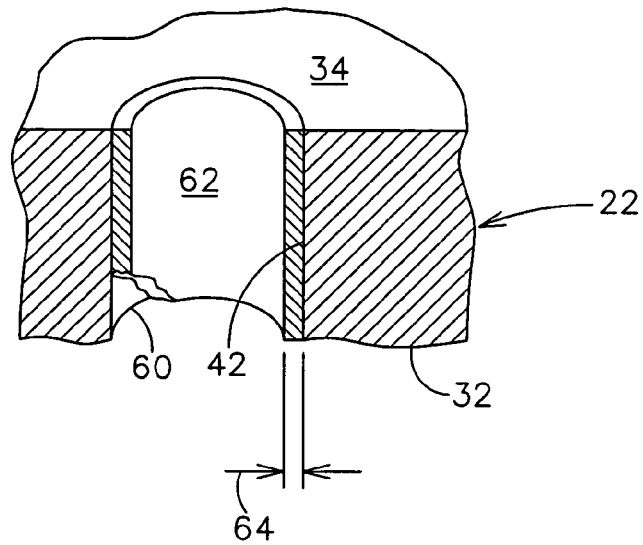
FIG. 3 is a further detail of a pore in the membrane portion of the apparatus.

As will be appreciated by those skilled in the art, an interior surface 60 defining each pore 42 may be coated with a coating 62 as illustrated in FIG. 3 so that individual particles (e.g., molecules) passing through the pore are likely to contact coating. For example, the pores 42 may be coated with a particular reagent so that desired reactions occur as the particles pass through the pores. Further, the coating 62 may be electrically charged if desired. Although the coatings 62 may have other thicknesses without departing from the scope of the present invention, in one embodiment the coating has a thickness 64 of about 10 nanometers. In one particular embodiment, the pore 42 is coated with gold by electroless deposition. Furthermore, the coating may comprise more than one component. In one embodiment the pore 42 is coated with gold by electroless deposition and the gold is subsequently derivatized with a linear chemical agent terminated with a mercaptan at one end and a selected chemical functional group at the other end.

As will be appreciated by those skilled in the art, the separations capacity factor, which is governed by the surface-to-volume ratio, can be quite large. For example, the separations capacity factor increases by about 120 times when a pore 42 having a width of about 200 nm is coated with a reagent having a thickness 64 of about 10 nm compared to a pore having a width of about 20 um coated with the same coating.

Although in one embodiment the fluid in the first and second channels 28, 30 have identical chemistries, the fluid in each channel may have different chemistries without departing from the scope of the present invention. As will be appreciated by those skilled in the art, each of the fluids contained by the channels 28, 30 has a Debye length which is a measure of the distance at which the Coulomb field of the charged particles in a plasma cease to interact. The properties of the flow through the pores 42 is affected by the relationship between the width 44 of the pores and the Debye length of the fluid in the channels 28, 30. In one embodiment, the first channel 28 is filled with a first fluid having a first Debye length and the second channel 30 is filled with a second fluid having a second Debye length at least as long as the first Debye length. Further, the pore 42 has a width 44 between about 0.01 and about 1000 times the first Debye length. If the pores have a small width (closer to 0.01 times the first Debye length), then flow in the pores is dominated by electroosmosis, whereas if the pores have a large width (greater than 1 first Debye length), then ion migration dominates the flow in the pores.

Figure 4:
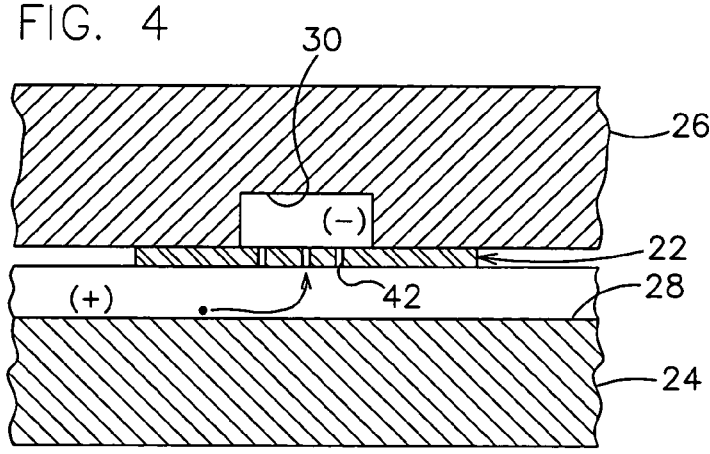
FIG. 4 is a schematic cross section of the apparatus of the present invention.

The previously described apparatus 20 can be used to selectively transfer one or more components of fluid from the first channel 28 to the second channel 30 as illustrated in FIG. 4. Fluid is delivered to the first and second channels 28, 30, respectively. An electrical potential is developed between the fluid in the first channel 28 and the fluid in the second channel 30 thereby causing one or more components of fluid (e.g., a particle) to pass through the pore 42 in the membrane 22.

In addition, the apparatus 20 may be used to tag a selected component within a fluid. A chemical reagent (e.g., an antibody) is passed through the pore 42 so the reagent coats the interior surface 60 of the pore. Alternatively a sequence of chemical reagents can be passed through the pore 42 so that a multilayer structure is built up to coat the interior surface 60 of the pore. The pore 42 is flushed to remove the reagent from a central portion of the pore so the reagent coats the surface 60 of the pore. The fluid component to be tagged is drawn through the pore 42 using a method such as described above so the selected component contacts the reagent coating 62, and a tagging reaction results between the selected component and the immobilized chemical reagent. Although it is envisioned other methods may be used to attract the selected component to the pore in one embodiment, the electrical potential between the fluid in channel 28 and the fluid in channel 30 draws the selected component through the pores. It is further envisioned that the membrane 22 may be selected so the pore 42 has a width 44 equal to between about 0.5 and about 100 times the Debye length of the fluid plus between about 1 and about 1000 times a width of the selected component.

Figure 5A:
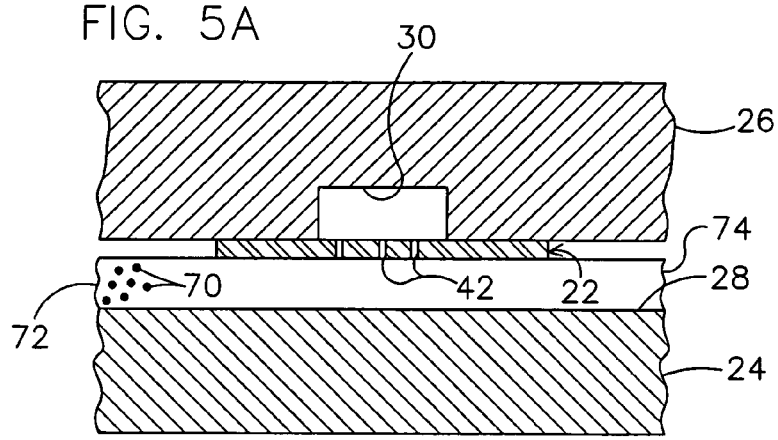
FIGS. 5a–5c are schematic cross sections of the apparatus illustrating a steps of a method of the present invention.
Figure 5B:
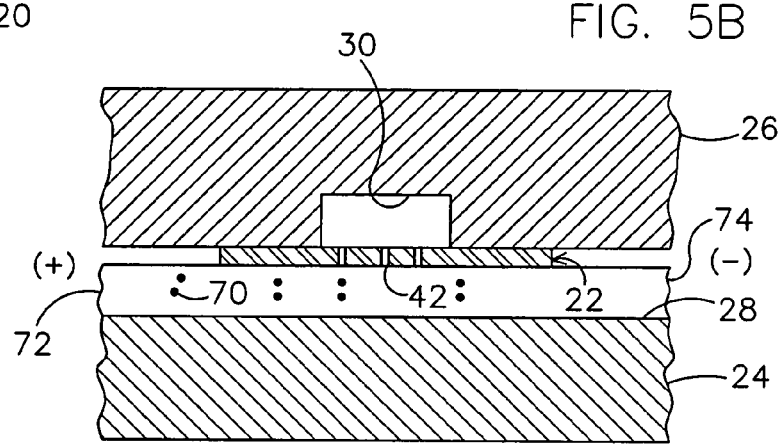
Figure 5C:
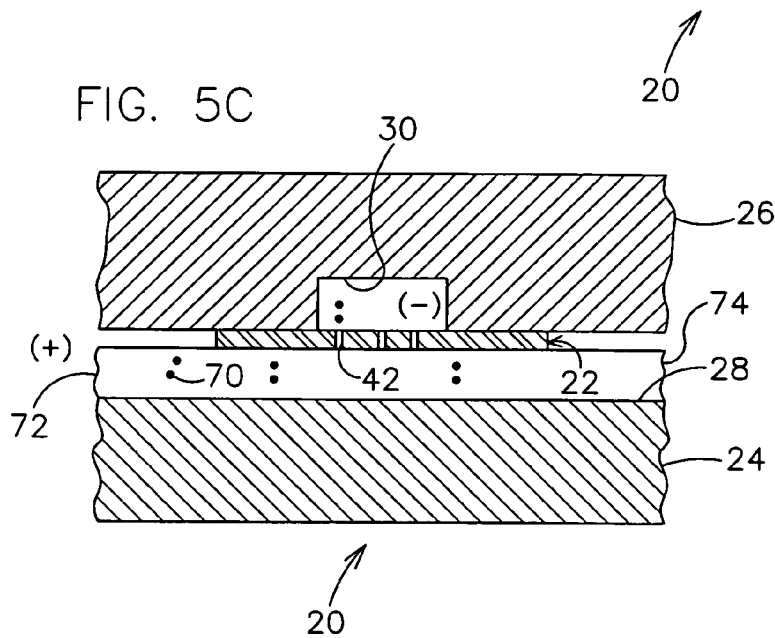

The previously described apparatus 20 also may be used to isolate a particle having a selected electrophoretic velocity from a plurality of particles. As illustrated in FIG. 5a, the first channel 28 is filled with a fluid, and the plurality of particles 70 are positioned in the fluid at a first end 72 of the first channel. An electrical potential is developed between the first end 72 of the first channel 28 and a second end 74 of the first channel opposite the first end so each of the plurality of particles 70 migrate along the first channel from the first end to the second end in an order corresponding to their respective electrophoretic velocities as shown in FIG. 5b. An electrical potential is developed between the first channel 28 and the second channel 30 when the particle having the selected electrophoretic velocity is adjacent the pores 42 in the membrane 33 so the particle passes through the pore from the first channel to the second channel as illustrated in FIG. 5c. Although the electrical potential may be switched nearly instantaneously from the former condition to the latter condition, in one embodiment the electrical potential is adjusted when the particle having the selected electrophoretic velocity is adjacent the pores 42 in the membrane 22 so the desired particle stops migrating along the first channel 28. Further, in one embodiment the electrical potential between the first channel 28 and the second channel 30 is adjusted once the particle having the selected electrophoretic velocity has passed through the pores 42 from the first channel to the second channel to prevent particles 70 having electrophoretic velocities other than the selected electrophoretic velocity from passing through the pore.

As will be understood by those skilled in the art, fluidic communication can be established among any number of vertically stacked bodies and each body can be adapted to perform a specialized fluid handling, separation or sensing task. Interconnects as described above can be used to provide controllable transport of components between bodies. It is further envisioned that such systems could be used to perform complex sequences and arrays of fluidic manipulations as will be explained in further detail below.

Using nanofluidic structures to connect microfluidic channels allows a variety of flow control concepts to be implemented, leading to hybrid fluidic architectures of considerable power and versatility. The key characteristic feature of nanofluidic channels is that fluid flow occurs in structures of the same size as physical parameters that govern the flow. For example, the Debye length which characterizes the length scale of ionic interactions in solution spans the range between about 1 nm and about 50 nm when the ionic strength of the buffer solution lies in the high-to-low mM range. Because the solution Debye length is of the order of the channel dimensions in the nanopores, fluidic transfer may be controlled through applied bias, polarity and density of the immobile nanopore surface charge, and the impedance of the nanopore relative to the microfluidic channels. Transfer between microchannels may be operated to produce either two or three stable transfer rates, illustrating the digital character of the fluidic transfer. Furthermore, the separations capacity factor governed by the surface-to-volume ratio, can be quite large. For example, the separations capacity factor is about 120 times larger for a pore having a width of about 200 nm and a coating thickness of about 10 nm compared to a pore having a width of about 20 um and the same coating.

Because gateable transfer of selected solution components between vertically separated microfluidic channels opens the way to multilevel fluidic systems, the potential applications of this technology are far reaching. As one example, the presence of high salt concentrations degrades electrophoretic separations. With this technology, one can pre-separate analytes from high-salt biological fluids, collect and concentrate particular fractions of the separation into a different layer now under optimum conditions for a high resolution second-dimensional separation. Because the manipulations are displaced vertically one could readily imagine multi-dimensional separations, not limited by the two in-plane spatial directions. One can even envision placing derivatizing chemistry or immunochemical reagents in a particular channel layer and allow chemical reactions to take place on a selected analyte band. Given the large variety of single layer devices already optimized to perform cellular manipulations, chemical reactions and complex separations, the ability to combine these individual architectures into independent layers with external control of the transfer of individually selectable analytes between layers, will enable many applications.

As will be appreciated by those skilled in the art, the direction of particle travel in the apparatus 20 can be controlled by applied potential, surface charge density (pH controllable), ionic strength, and even by the impedance of the fluidic network in which the interconnect is placed relative to the impedance of the membrane 42.

The present invention has been demonstrated through the following examples:

EXAMPLES

The simple system described above was formed as a proof of concept. Microfluidic channels were formed in bodies of polydimethylsiloxane (PDMS) using standard rapid prototyping protocols for PDMS as explained in J. C. McDonald, et al., *Electrophoresis* 21, 27–40 (2000). A 5 um thick nanoporous membrane was sandwiched between the bodies. Assembly has been accomplished by centering a 10 mm×1 mm section of membrane on the lower body and placing the upper body on the membrane so its channel was perpendicular to the channel in the lower body.

More sophisticated embodiments of the hybrid microfluidic and nanofluidic system, such as a seven layer sandwiched structure, may be made using the following protocol:

(1) Etch microchannels and holes in a glass substrate.

(2) Mount a polycarbonate nanopore membrane having desired pore diameters on a carrier, such as a PDMS slab about 2 mm thick, without wrinkling or deforming and sufficiently to hold the membrane in place for subsequent handling, but not so tightly as to permanently bond the membrane to the carrier.

(3) Apply adhesive type B (as described below) to the substrate with imprinting, spraying, or screening techniques.

(4) Align the membrane and carrier to the etched glass substrate and tack them in place.

(5) Release the carrier from the membrane leaving it on the substrate to form a layered stack.

(6) Repeat step (2) to a solid polycarbonate membrane layer.

(7) Using conventional shadow mask, etch a desired pattern of channels and holes into the solid membrane using reactive oxygen ion etching, or similar etching techniques for polymers.

(8) Apply adhesive type H (as described below) to the solid membrane, with imprinting, spraying or screening techniques.

(9) Align the patterned solid membrane with the stack and tack the membrane in place.

(10) Repeat step (2) to the second nanopore PC membrane

(11) With shadow mask, etch desired holes and/or channels into membrane.

(12) Apply adhesive type H to the substrate.

(13) Repeat steps (4) & (5).

(14) Repeat steps (6) to (9) for a second solid PC membrane.

(15) Repeat steps (10) to (13) for a third nanopore PC membrane.

(16) Apply adhesive type B to a top glass layer having desired etched holes and channels.

(17) Apply pressure to the entire stack and heat to thermally cure and activate the adhesives, without degrading the polycarbonate.

Figure 8:
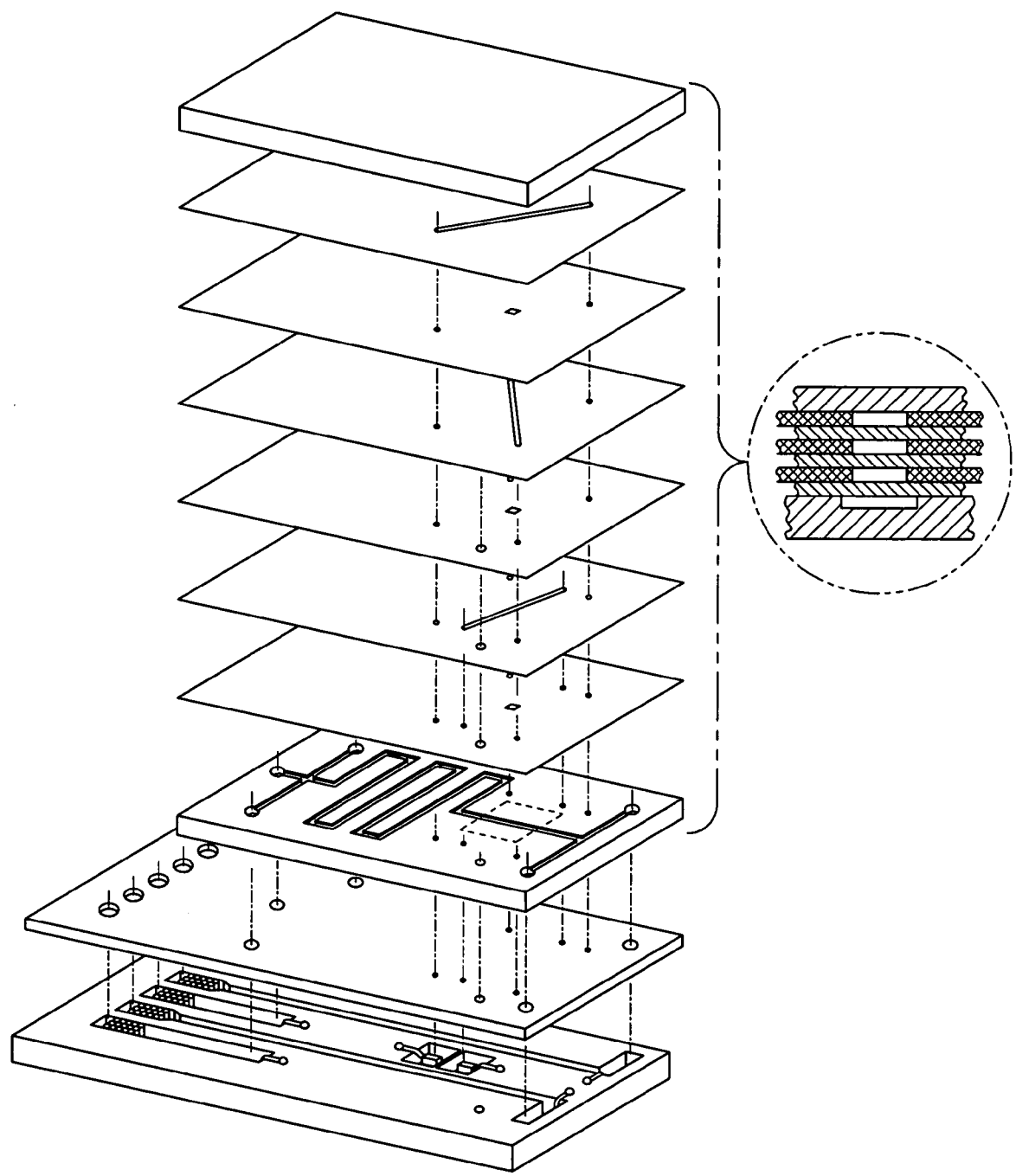
FIG. 8 is a separated perspective of a second apparatus of the present invention.
Figure 9A:
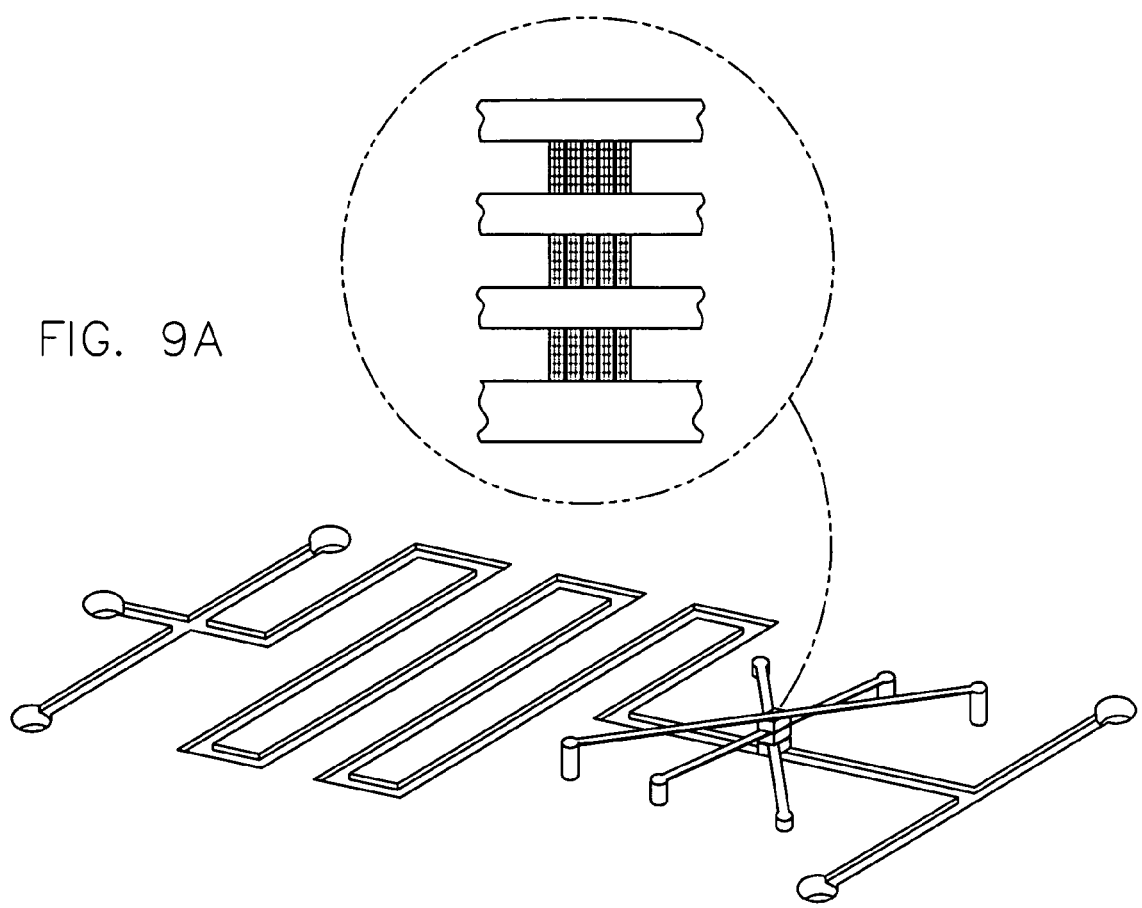
FIG. 9a is a perspective showing a fluid circuit formed by the second apparatus.
Figure 9B:
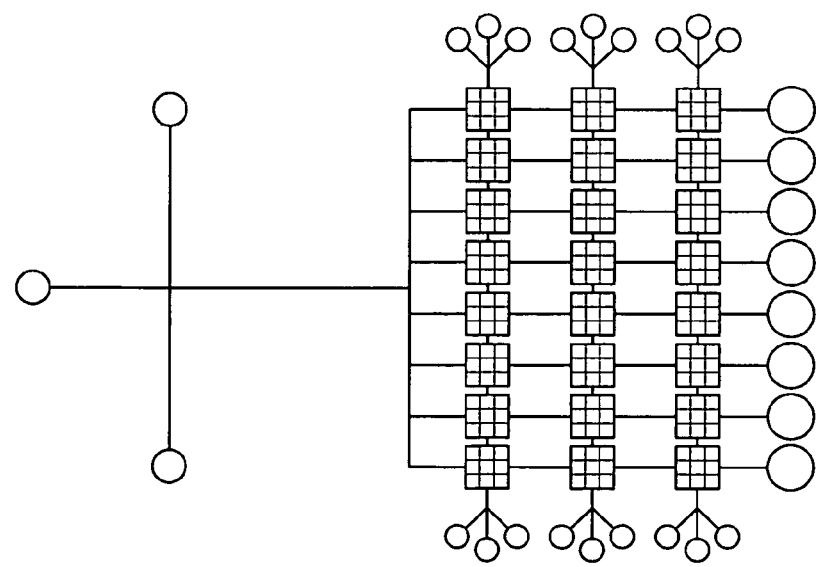
FIG. 9b is a schematic showing an array of fluid circuits formed from an expansion of the second apparatus.

A separated view of the resulting apparatus made by this protocol is shown in FIG. 8. FIG. 9a illustrates the resulting fluid circuit. It is further envisioned that such circuits could be assembled to perform complex sequences and arrays of fluidic manipulations as illustrated in FIG. 9b.

One of the keys to achieving the desired bond is to use adhesives that can be dried of solvents after application, and that can be thermally cured without evolving sufficient vapors that produce undesired bubbles in the bond. For the glass/polycarbonate combination, adhesive B is a phenolic-based adhesive that is soluble in various non-aqueous solvents, such as ethanol. For the polycarbonate/polycarbonate combination, adhesive H is a low molecular weight polycarbonate dissolved in solution. For both adhesives, the adhesives are diluted to a low concentration, so that the bond thickness on cure is 1 to 2 micrometers thick. If too thick of an adhesive layer is applied, the adhesive on curing can reflow back into the microfluidic channels and potentially plug the channels and nanopores. The bonds are then created by applying pressure and heat, typically over 100 psi and under 150° C. The process steps are still under development to determine the optimum bond cycles.

Figure 6A:
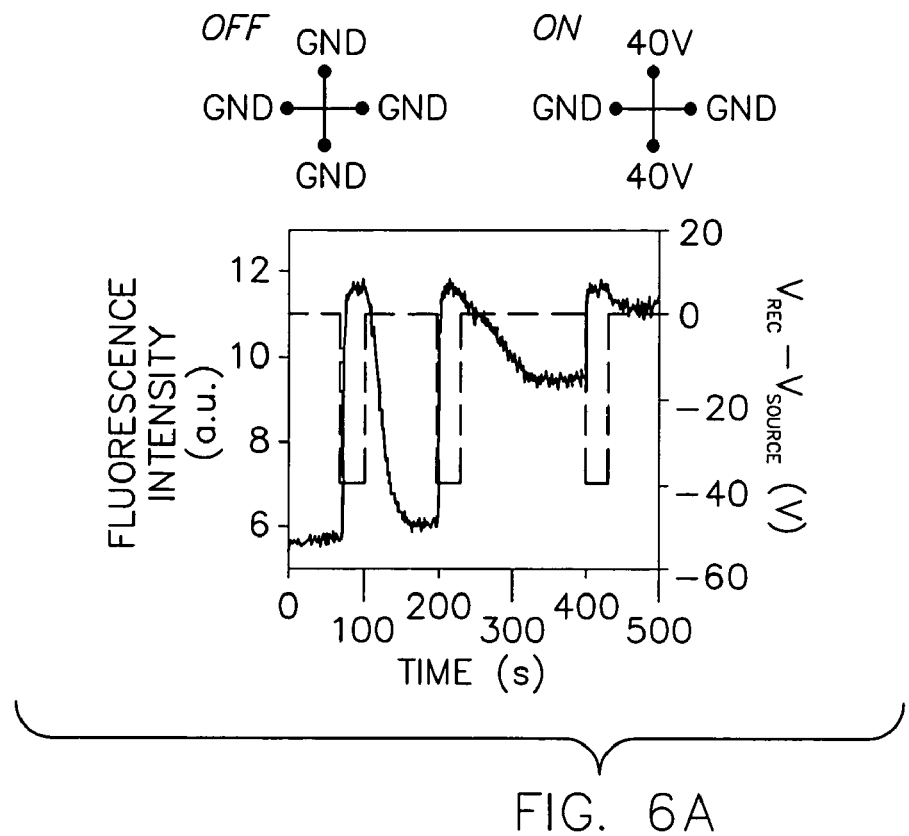
Figure 6B:
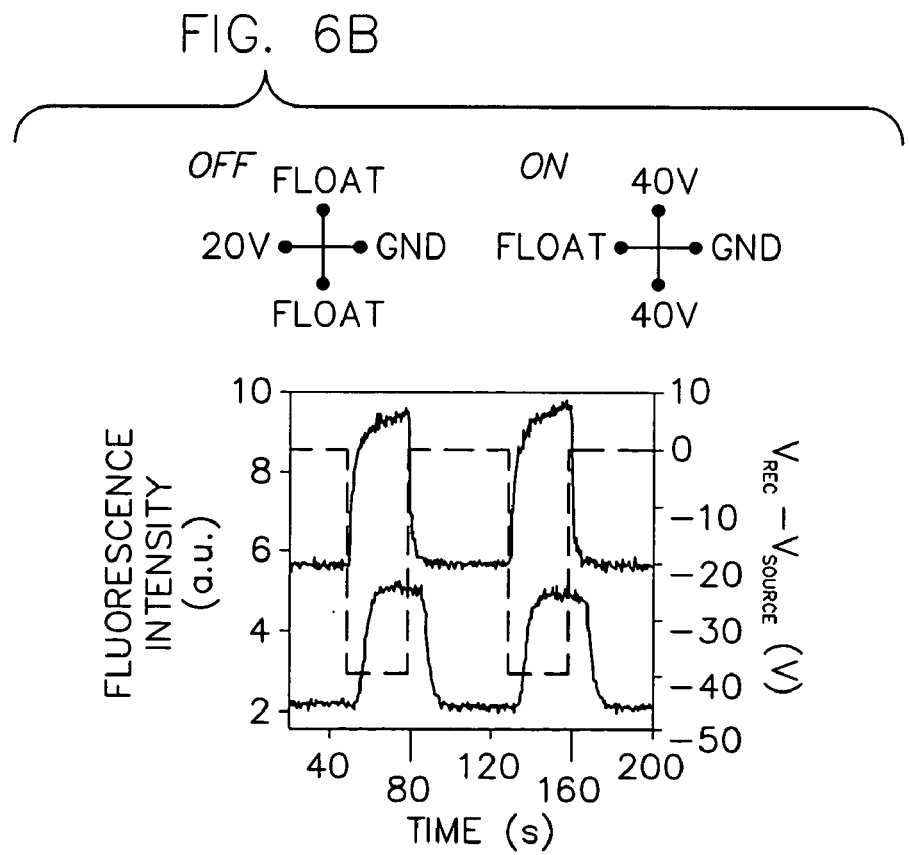

The crossed microfluidic channels spatially define the transport region and eliminate the need for precise alignment of the nanofluidic membrane. Transport control was monitored with fluorescence spectroscopy and imaging of fluid streams containing small molecule fluorophores by interrogating the fluorescence signal on either the originating or the receiving channel side of the nanofluidic membrane. FIG. 6a shows the transfer of an aqueous 5 mM phosphate buffer solution, PBS pH=8, of the anionic fluorophore, fluorescein, across a 200 nm pore diameter polycarbonate, PCTE, membrane to a receiving channel held under static, i.e. flow-free, conditions. Successive transfers were affected by application of negative bias pulses. Because the receiving channel was held static, the fluorophore concentration probed during bias application was a balance between active transport from the source channel and diffusion along the receiving channel. When the bias was removed, diffusion depleted the concentration in the region probed, but with successive forward bias applications the concentration of probe in the receiving channel increased, thereby diminishing the driving force for diffusion after subsequent transfers. FIG. 6b shows a similar experiment in which active flow was maintained in the receiving channel. The build-up to steady-state at the membrane after bias application results from the balance between active transport of the analyte across the nanofluidic membrane and its removal by cross-flow in the receiving channel, which is clearly more gradual than under static conditions. An obvious time offset was observed when the detection region was moved downstream of the interconnect. FIG. 6c demonstrates the level of control and speed of transfer possible with these nanofluidic interconnects. In this experiment the off-state voltages were allowed to float, producing a non-zero level of transfer intermediate between the forward-bias (−60 V) on-state and the reverse-bias (+60 V) on-state. Measurements on the changing edges of FIG. 6c indicate steady state concentration was re-established in the receiver channel within ~1.2 s of applying the switching voltage. FIG. 6d demonstrates the insensitivity to charge state by comparing the transfer of the neutral fluorophore, 4,4-difluoro-5,7-dimethyl-4-bora-3a,4a-diaza-s-indacene-3-succinimidylpropionate (bodipy).

In all of the above experiments the direction of transfer was controlled by the electroosmotic flow generated by the microfluidic channels. PDMS exhibits a negative surface charge at pH=8, so forward bias is expected when $V_{rec}-V_{source}<0$, as observed. Interestingly, this is directly opposite to the flow direction based on the electroosmotic flow characteristics of the PCTE membrane alone. The surfaces of the PCTE membrane channels are coated with polyvinylpyrrolidone (PVP) to render them hydrophilic. The tertiary amine of the PVP is susceptible to protonation, making the surface net positive at pH 8, thus recruiting a population of negative solution counterions to the interior of the nanochannels. Under the low ionic strength conditions used here, the ionic population in the channel is predominantly $H_2PO_4^-/HPO_4^{2-}$, so forward bias is obtained with $V_{rec}-V_{source}>0$, if the nanofluidic channels control the direction of transport. Instead, flow in the direction predicated on the (negative) charge state of the PDMS surfaces of the microfluidic channels controls transport.

Figure 7A:
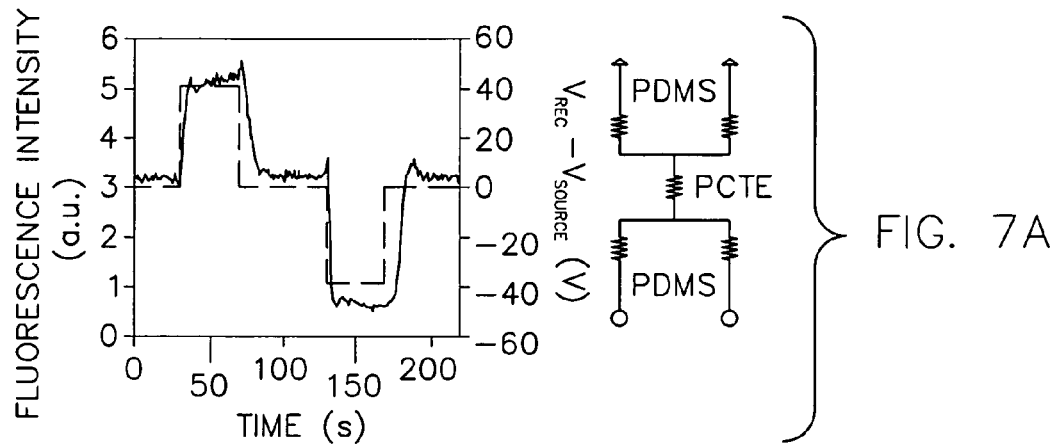
FIGS. 7a–7c are fluorescence signature graphs for various experimental transfers.
Figure 7B:
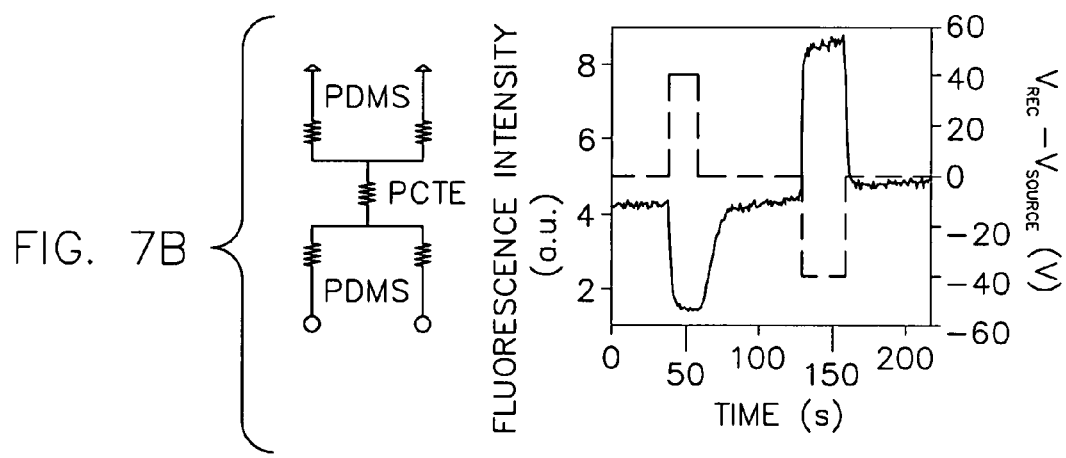

This control can be reversed, as shown in FIGS. 7a and 7b, for transport across a 200 nm pore diameter membrane compared with that across a 15 nm pore diameter membrane. Clearly the polarities of forward- and reverse-bias have been reversed. This behavior can be understood based on two effects—the greatly increased resistance to pressure driven flow through the smaller pores and the greater voltage drop across the pores in the 15 nm case. Modeling the impedance network composed of the two microfluidic channels and the membrane shows that in the network containing the 200 nm pore membrane<2% of the potential is dropped across the nanofluidic membrane. However, for 15 nm pores, just over 33% of the potential appears across the membrane, so that the PCTE pore electroosmotic flow dominated overall fluid transport in the device when 15 nm pores were used, but not when larger pores were employed. Thus, by choosing the pore size, pore and channel surface chemistries, and solution composition, one can select either direction of fluid flow for the same externally applied voltage.

Figure 7C:
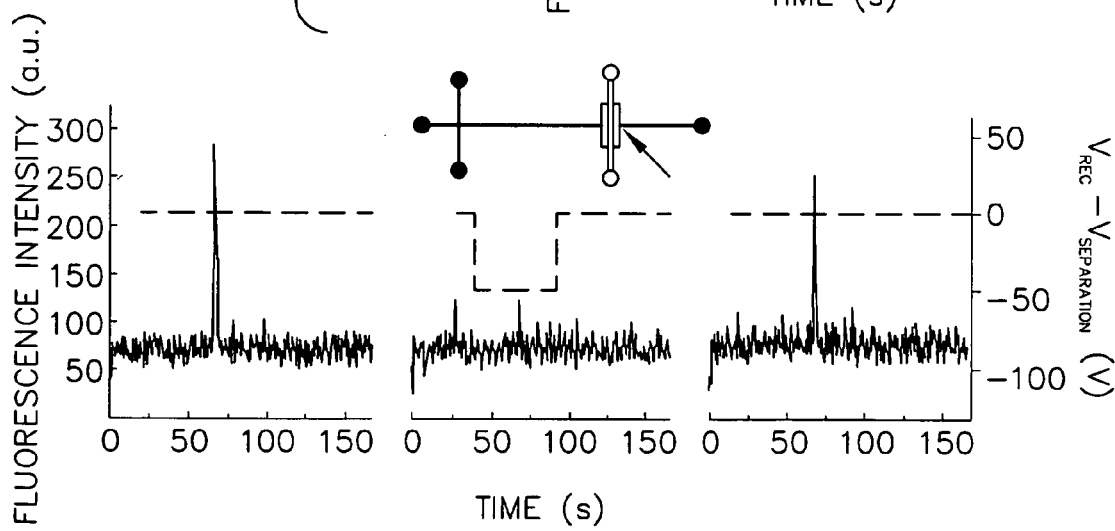

These control concepts have been used to effect preparative separations on the microscale by incorporating them into a microfabricated capillary electrophoresis arrangement with a molecular gate membrane placed between two channel layers just before the detection region. When the gate is off, the system acts as a standard electrophoresis system; when the gate is forward biased, the analyte is collected in the vertically displaced receiving channel, and the signal is reduced or eliminated at the detection region. FIG. 7c shows three successive injections of a fluorescein-containing plug in the flow-injection analysis scheme. The inset to FIG. 7c shows a schematic diagram of the preparative electrophoresis apparatus. The horizontal channel forms the main separation (electrophoresis) channel with the left-hand vertical channel provided to provide for injection of a sample mixture onto the channel for separation. The right-hand vertical channel is held in a separate vertical plane and is separated from the main electrophoresis channel by a molecular gate membrane (denoted by the vertical rectangle at the crossing point of the vertical and horizontal channels). The sample bands are all labeled with a fluorescent tag, and are detected in the horizontal electrophoresis channel just after they pass the molecular gate membrane. When no sampling gate pulse was applied (left panel), the fluorescein is transported past the membrane gate collection region. Application of a negative gate pulse to the 200 nm pore diameter polyvinylpyrrolidone free (PVPF) membrane (middle panel) results in nearly complete removal of the analyte band from the electrophoresis channel. Another injection made with no gate pulse reproduces the results of the initial injection. In this experiment a PVPF membrane consisting of pores with negative surface charge was used, so the polarity of transfer was the same as that based on the PDMS microchannels.

Among the advantages of the apparatus 20 of the present invention is the ability to selectively control flow by controlling the potential applied across the pores 42. Flow through the pores 42 can be started and stopped nearly instantaneously. Systems can be created in which the flow is normally on or off until a potential is applied between the fluids in the two channels. Further, direction of flow through the pores 42 can be instantaneously reversed. Still further, the apparatus 20 allows certain species to be selectively transported or blocked from passage through pores 42 and selected pores within the apparatus 20 can be controlled using the fluids themselves as the signal path.

Surface charge density is a critical property influencing electrokinetic flow in these structures, because the enhanced surface-to-volume ratio in these nanofluidic channels means that a significant fraction of the total charge is bound to the walls and is immobile. Because it determines the magnitude of the surface potential and the applicability of the Debye-Hückel approximation, surface charge density provides an experimental handle to adjust the microscopic processes that determine transport in the nanopore. Thus, the potential for facile control of nanofluidic flow by varying the bias, nanochannel wall charge density, charge polarity, and/or solution ionic strength offers the opportunity to effect intelligent transfer of fluid components with extreme ease and versatility.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A fluid circuit comprising:
    a membrane having a first side, a second side opposite said first side, and a pore extending from said first side to said second side;
    a first channel containing fluid extending along said first side of the membrane;
    a second channel containing fluid extending along said second side of the membrane and forming a crossing with said first channel; and
    an electrical source in electrical communication with at least one of said first fluid and second fluid for selectively developing an electrical potential between fluid in said first channel and fluid in said second channel thereby causing at least one component of fluid to pass through the pore in the membrane at said crossing from one of said first channel and said second channel to the other of said first channel and said second channel;
    wherein the membrane has a thickness of between about 1 micrometer and about 100 micrometers.

2. A fluid circuit as set forth in claim 1 wherein said second channel extends generally perpendicular to said first channel.

3. A fluid circuit as set forth in claim 1 wherein said pore has a width less than about 250 nanometers.

4. A fluid circuit as set forth in claim 3 wherein said pore has a width between about 10 nanometers and about 230 nanometers.

5. A fluid circuit as set forth in claim 4 wherein said pore has a width between about 15 nanometers and about 220 nanometers.

6. A fluid circuit as set forth in claim 1 wherein said pore is generally cylindrical.

7. A fluid circuit as set forth in claim 1 wherein said pore is a first pore of a plurality of pores.

8. A fluid circuit as set forth in claim 7 wherein said membrane has a pore density of between about 1,000,000 pores per square centimeter and about 10,000,000,000 pores per square centimeter.

9. A fluid circuit as set forth in claim 8 wherein said membrane has a pore density of between about 100,000,000 pores per square centimeter and about 600,000,000 pores per square centimeter.

10. A fluid circuit as set forth in claim 1 wherein the membrane has a thickness of about 10 micrometers.

11. A fluid circuit as set forth in claim 1 wherein the pore is defined by an internal surface and the membrane includes a coating extending along the internal surface.

12. A fluid circuit as set forth in claim 11 wherein the coating includes an electrical charge.

13. A fluid circuit as set forth in claim 11 wherein the coating comprises a plurality of distinct chemical layers.

14. A fluid circuit as set forth in claim 11 wherein the coating has a thickness of about 10 nanometers.

15. A fluid circuit as set forth in claim 1 wherein the pore is defined by an internal surface and the membrane includes a gold coating extending along the internal surface.

16. A fluid circuit as set forth in claim 1 wherein the pore is defined by an internal surface and the membrane includes a gold coating extending along the internal surface and a layer formed on the gold coating by chemisorption of a mercaptan-terminated chemical agent.

17. A fluid circuit as set forth in claim 1 wherein fluid in said first channel and said second channel have different chemistries.

18. A fluid circuit as set forth in claim 1 wherein the electrical potential developed by the electrical source is between about 10 millivolts and about 200 volts.

19. A fluid circuit comprising:
a membrane having a first side, a second side opposite said first side, and a pore extending from said first side to said second side having a width less than about 250 nanometers;
a first channel containing fluid extending along said first side of the membrane; and
a second channel containing fluid extending along said second side of the membrane and forming a crossing with said first channel;
wherein the membrane has a thickness of between about 1 micrometer and about 100 micrometers, and
the pore in the membrane is at said crossing.

20. A fluid circuit as set forth in claim 19 wherein said second channel extends generally perpendicular to said first channel.

21. A fluid circuit as set forth in claim 19 wherein said pore has a width between about 10 nanometers and about 230 nanometers.

22. A fluid circuit as set forth in claim 21 wherein said pore has a width between about 15 nanometers and about 220 nanometers.

23. A fluid circuit as set forth in claim 19 wherein said pore is generally cylindrical.

24. A fluid circuit as set forth in claim 19 wherein said pore is a first pore of a plurality of pores.

25. A fluid circuit as set forth in claim 24 wherein said membrane has a pore density of between about 1,000,000 pores per square centimeter and about 10,000,000,000 pores per square centimeter.

26. A fluid circuit as set forth in claim 25 wherein said membrane has a pore density of between about 100,000,000 pores per square centimeter and about 600,000,000 pores per square centimeter.

27. A fluid circuit as set forth in claim 19 wherein the membrane has a thickness of about 10 micrometers.

28. A fluid circuit as set forth in claim 19 wherein the pore is defined by an internal surface and the membrane includes a coating extending along the internal surface.

29. A fluid circuit as set forth in claim 28 wherein the coating includes an electrical charge.

30. A fluid circuit as set forth in claim 28 wherein the coating comprises a plurality of distinct chemical layers.

31. A fluid circuit as set forth in claim 28 wherein the coating has a thickness of about 10 nanometers.

32. A fluid circuit as set forth in claim 19 wherein the pore is defined by an internal surface and the membrane includes gold coating extending along the internal surface.

33. A fluid circuit as set forth in claim 19 wherein the pore is defined by an internal surface and the membrane includes a gold coating extending along the internal surface and a layer formed on the gold coating by chemisorption of a mercaptan-terminated chemical agent.

34. A fluid circuit as set forth in claim 19 wherein fluid in said first channel and said second channel have different chemistries.

35. A fluid circuit comprising:
a membrane having a first side, a second side opposite said first side, and a pore extending from said first side to said second side;
a first channel containing a first fluid having a first Debye length in fluid communication with said first side of the membrane; and
a second channel containing a second fluid having a second Debye length at least as long as said first Debye length in fluid communication with said second side of the membrane and forming a crossing with said first channel;
wherein the pore has a width between about 0.01 and about 1000 times the first Debye length;
the membrane has a thickness of between about 1 micrometer and about 100 micrometers, and
the pore in the membrane is at said crossing.

36. A fluid circuit as set forth in claim 35 further comprising an electrical source in electrical communication with at least one of said first fluid and second fluid for selectively developing an electrical potential between said first fluid and said second fluid thereby causing at least one component of at least one of said first fluid and said second fluid to pass through the pore in the membrane from one of said first channel and said second channel to the other of said first channel and said second channel.

37. A fluid circuit as set forth in claim 36 wherein the electrical potential developed by the electrical source is between about 10 millivolts and about 200 volts.

38. A fluid circuit as set forth in claim 35 wherein said second channel extends generally perpendicular to said first channel.

39. A fluid circuit as set forth in claim 36 wherein said pore has a width less than about 250 nanometers.

40. A fluid circuit as set forth in claim 39 wherein said pore has a width between about 10 nanometers and about 230 nanometers.

41. A fluid circuit as set forth in claim 40 wherein said pore has a width between about 15 nanometers and about 220 nanometers.

42. A fluid circuit as set forth in claim 35 wherein said pore is generally cylindrical.

43. A fluid circuit as set forth in claim 35 wherein said pore is a first pore of a plurality of pores.

44. A fluid circuit as set forth in claim 43 wherein said membrane has a pore density between about 1,000,000 pores per square centimeter and about 10,000,000,000 pores per square centimeter.

45. A fluid circuit as set forth in claim 44 wherein said membrane has a pore density between about 100,000,000 pores per square centimeter and about 600,000,000 pores per square centimeter.

46. A fluid circuit as set forth in claim 35 wherein the membrane has a thickness of about 10 micrometers.

47. A fluid circuit as set forth in claim 35 wherein the pore is defined by an internal surface and the membrane includes a coating extending along the internal surface.

48. A fluid circuit as set forth in claim 47 wherein the coating includes an electrical charge.

49. A fluid circuit as set forth in claim 47 wherein the coating comprises a plurality of distinct chemical layers.

50. A fluid curcuit as set forth in claim 47 wherein the coating has a thickness of about 10 nanometers.

51. A fluid circuit as set forth in claim 35 wherein the pore is defined by an internal surface and the membrane includes a gold coating extending along the internal surface.

52. A fluid circuit as set forth in claim 35 wherein the pore is defined by an internal surface and the membrane includes a gold coating extending along the internal surface and a layer formed on the gold coating by chemisorption of a mercapten-terminated chemical agent.

53. A fluid circuit as set forth in claim 35 wherein fluid in said first channel and said second channel have different chemistries.

54. An apparatus comprising:
a membrane having a first side, a second side opposite said first side, and a pore extending from said first side to said second side;
a first channel adjacent said first side of the membrane for containing fluid in fluid communication with said first side of the membrane;
a second channel adjacent said second side of the membrane for containing fluid in fluid communication with said second side of the membrane and forming a crossing with said first channel; and
an electrical source in electrical communication with at least one of said first channel and second channel for selectively developing an electrical potential between fluid in said first channel and fluid in said second channel thereby causing at least one said first channel and said second channel to the other of said first channel and said second channel;
wherein the membrane has a thickness of between about 1 micrometer and about 100 micrometers.

55. An apparatus as set forth in claim 53 wherein said second channel extends generally perpendicular to said first channel.

56. An apparatus as set forth in claim 54 wherein said pore has a width less than about 250 nanometers.

57. An apparatus as set forth in claim 56 wherein said pore has a width between about 10 nanometers and about 230 nanometers.

58. An apparatus as set forth in claim 57 wherein said pore has a width between about 15 nanometers and about 220 nanometers.

59. An apparatus as set forth in claim 54 wherein said pore is generally cylindrical.

60. An apparatus as set forth in claim 54 wherein said pore is a first pore of a plurality of pores.

61. An apparatus as set forth in claim 60 wherein said membrane has a pore density of between about 1,000,000 pores per square centimeter and about 10,000,000,000 pores per square centimeter.

62. An apparatus as set forth in claim 60 wherein said membrane has a pore density of between about 100,000,000 pores per square centimeter and about 600,000,000 pores per square centimeter.

63. An apparatus as set forth in claim 54 wherein the membrane has a thickness of about 10 micrometers.

64. An apparatus as set forth in claim 54 wherein the pore is defined by an internal surface and the membrane includes a coating extending along the internal surface.

65. An apparatus as set forth in claim 64 wherein the coating includes an electrical charge.

66. An apparatus as set forth in claim 65 wherein the coating comprises a plurality of distinct chemical layers.

67. An apparatus as set forth in claim 65 herein the coating has a thickness of about 10 nanometers.

68. An apparatus as set forth in claim 54 wherein the pore is defined by an internal surface and the membrane includes a gold coating extending along the internal surface.

69. An apparatus as set forth in claim 54 wherein the pore is defined by an internal surface and the membrane includes a gold coating extending along the internal surface and a layer formed on the gold coating by chemisorption of a mercaptan-terminated chemical agent.

70. An apparatus as set forth in claim 54 wherein the electrical potential developed by the electrical source is between about 10 millivolts and about 200 volts.

71. An apparatus comprising:
a plurality of membranes, each of said membranes having a first side, a second side opposite said first side, and a pore extending from said first side to said second side;
a plurality of pairs of channels, each of said pairs of channels including a first channel adjacent at least one of said first sides of the membranes for containing fluid in fluid communication with said first side of the respective membrane and a second channel adjacent at least one of said second sides of the membranes for containing fluid in fluid communication with said second side of the respective membrane, said second channel forming a crossing with said first channel; and
an electrical source in electrical communication with at least one of said channels for selectively developing an electrical potential between fluid in said channels thereby causing at least one component of fluid to pass through the pore in at least one of said membranes at said crossing;
wherein each of said membranes has a thickness of between about 1 micrometer and about 100 micrometers.

* * * * *

UNITED STATES PATENT AND TRADEMARK OFFICE
CERTIFICATE OF CORRECTION

PATENT NO.       : 7,220,345 B2
APPLICATION NO.  : 10/273935
DATED            : May 22, 2007
INVENTOR(S)      : Paul W. Bohn et al.

It is certified that error appears in the above-identified patent and that said Letters Patent is hereby corrected as shown below:

In the claims:

Column 13
In claim 54, line 16, after "one" insert --component of fluid to pass through the pore in the membrane at said crossing from one of--.
In claim 55, line 1, please delete "53" and insert --54--.

Signed and Sealed this

Twentieth Day of November, 2007

JON W. DUDAS
*Director of the United States Patent and Trademark Office*